United States Patent [19]
Field et al.

[11] Patent Number: 5,472,317
[45] Date of Patent: Dec. 5, 1995

[54] MOUNTING CLIP FOR A MEDICATION INFUSION PUMP

[75] Inventors: Jeffrey F. Field, North Hills; Heather M. Savage, Ventura, both of Calif.

[73] Assignee: MiniMed Inc., Sylmar, Calif.

[21] Appl. No.: 253,387

[22] Filed: Jun. 3, 1994

[51] Int. Cl.⁶ .............................. F04B 21/00; A61M 1/00
[52] U.S. Cl. ........................... 417/234; 224/252; 224/271; 604/131
[58] Field of Search ............................ 417/234; 224/252, 224/253, 269, 271; 604/131, 151

[56] References Cited

U.S. PATENT DOCUMENTS

| | | | |
|---|---|---|---|
| 4,444,548 | 4/1984 | Anderson et al. | 417/234 |
| 4,741,074 | 5/1988 | Budano, II et al. | 224/252 |
| 5,081,709 | 1/1992 | Benyo et al. | 224/252 |
| 5,370,622 | 12/1994 | Livingston et al. | 604/131 |

*Primary Examiner*—Charles Freay
*Attorney, Agent, or Firm*—Kelly, Bauersfeld & Lowry

[57] ABSTRACT

A mounting clip is provided for removable mounting of a medication infusion pump of the type used to deliver a selected medication such as insulin to a patient. In the preferred form, the mounting clip comprises a belt clip with a pair of pivotally interconnected and spring-loaded legs adapted for mounting onto a belt or other item of clothing worn by a patient. One leg of the belt clip includes a dovetail key for slide-fit reception into a mating dovetail slot formed in the housing of a medication infusion pump. A detent button is carried on the belt clip at the distal end of a spring arm for snap-fit reception into a detent seat formed in the pump housing, to lock the pump onto the belt clip. The spring arm is manually accessible to permit fingertip retraction of the detent button from the seat, and thereby permit easy sliding removal of the pump housing from the belt clip.

20 Claims, 3 Drawing Sheets

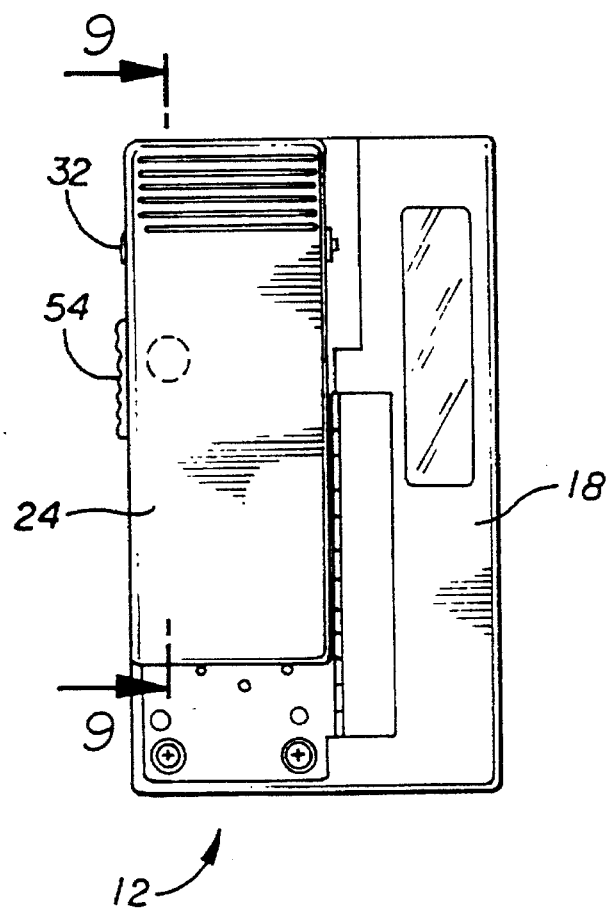
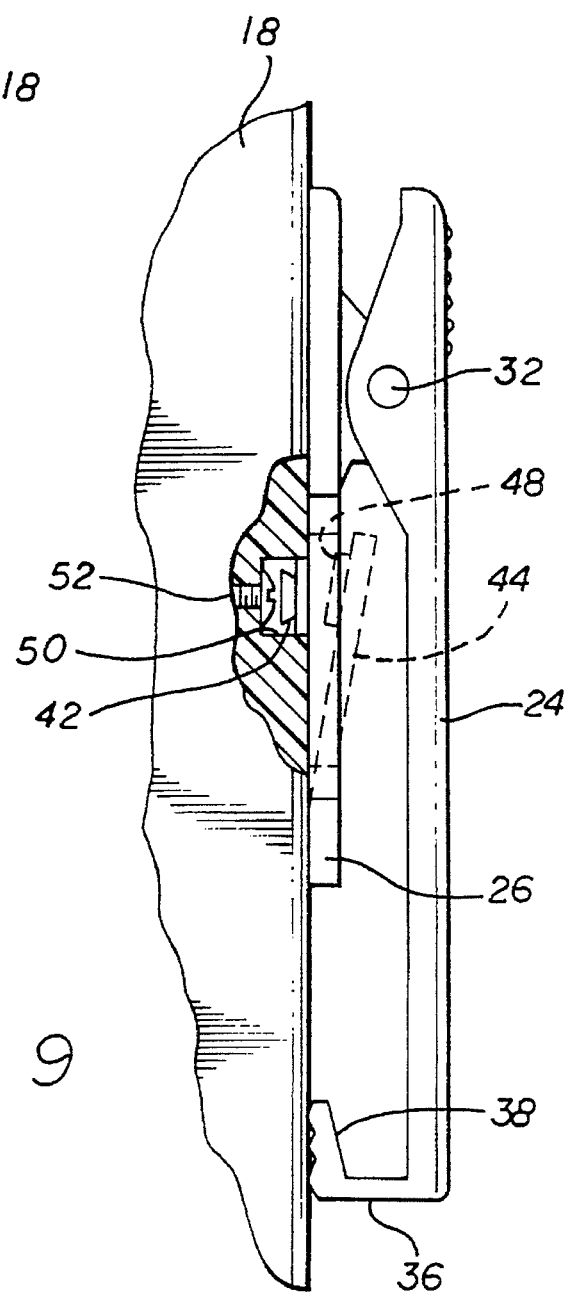
FIG. 8
FIG. 9

MOUNTING CLIP FOR A MEDICATION INFUSION PUMP

BACKGROUND OF THE INVENTION

This invention relates generally to an improved and relatively simple mounting clip for receiving and supporting a compact medication infusion pump from a belt or other clothing item worn by a patient. The mounting clip includes interlocking components designed for relatively quick and easy sliding and snap-fit removable mounting of an infusion pump.

Medication infusion pumps are generally known in the art for use in delivering or dispensing a prescribed medication to a patient. In one common form, such devices comprise a relatively compact pump housing adapted to receive a syringe carrying a prescribed medication for administration to a patient through a catheter or the like. The infusion pump includes a small drive motor for controlled advancement of a syringe piston plunger to administer the medication to the patient. Programmable control means are normally provided for operating the drive motor continuously or at periodic intervals to obtain a closely controlled and accurate delivery of medication over an extended period of time. Such infusion pumps are utilized to administer insulin and other medications, with exemplary pumps being marketed by MiniMed Technologies of Sylmar, Calif. under model designations 504 and 506. See also U.S. Pat. Nos. 4,562,751; 4,678,408; and 4,685,903.

Medication infusion pumps of the general type described above provide significant advantages and benefits with respect to accurate delivery of the medication over an extended period of time. The infusion pump is often designed to be extremely compact and thus may be adapted to be carried by the patient. As a result, the medication can be administered with precision and in an automated manner, without significant restriction on the patient's mobility or life-style.

In the past, compact medication infusion pumps have been adapted for mounting onto a patient's belt or other selected clothing item, by means of a conventional spring-legged belt clip. In this regard, such belt clip devices have typically been designed for connection to the housing of the infusion pump, and for clip-on installation onto the patient's belt. However, manipulation of the pump housing and belt clip for this purpose is a difficult maneuver for many patients to perform in a smooth and controlled manner without rapid or jerking motions. In this regard, it is important for the patient to avoid significant tension applied to the catheter, to correspondingly avoid inadvertent disruption of medication delivery. Conventional belt clips have not been designed to safeguard against rapid or jerking motions during pump mounting or removal, whereby great care must be exercised by the patient to prevent excessive tension forces on the catheter.

The present invention overcomes the problems and disadvantages of the prior art, by providing an improved mounting or belt clip adapted for quick and easy mounting of a medication infusion pump onto and subsequent removal of the pump from a patient's belt or the like, without requiring any rapid motions.

SUMMARY OF THE INVENTION

In accordance with the invention, a mounting clip is provided for removably mounting a medication infusion pump onto a belt or the like worn by a patient. The mounting clip includes means for slide-fit and snap-fit locking engagement with the housing of a medication infusion pump to permit pump mounting onto and removal from the clip in a safe and controlled manner.

In the preferred form of the invention, the mounting clip comprises a belt clip having a pair of pivotally interconnected and spring-loaded legs adapted for clamp-on mounting onto the belt or similar article of clothing worn by a patient. The belt clip legs are adapted to be manually squeezed together at one end to displace the opposite ends away from each other, thereby facilitating mounting of the belt clip onto or removal of the belt clip from the patient's belt.

One of the belt clip legs, disposed at the outboard side of the patient's belt, comprises a mounting plate for removably supporting the pump. In the preferred form, this mounting plate includes a dovetail key for slide-fit reception into a matingly shaped dovetail slot formed in the housing of the medication infusion pump. The dovetail key and slot thus permit slide-on mounting and slide-off removal of the pump housing.

The outboard leg of the mounting clip also includes a spring arm with a detent button formed on the distal end thereof. The detent button is positioned for snap-fit reception into a detent recess or seat formed on the pump housing, when the dovetail key and slot are fully engaged. In the preferred form, the detent button is located adjacent to and generally in-line with the dovetail key, for snap-fit reception into the detent seat which may conveniently comprise a shallow counterbore for receiving a mounting screw used to assemble portions of the pump housing. The pump housing is smoothly and easily installed onto the mounting clip by moving the pump housing in a manner slidably receiving the dovetail key into the dovetail slot. As the dovetail key and slot approach full engagement, the detent button engages a corner of one side edge of the pump housing and rides thereover for snap-fit locking reception into the detent seat. When the pump is fully installed, a serrated edge of the spring arm protrudes beyond the adjacent side edge of the pump housing to permit fingertip retraction of the spring arm and the detent button relative to the detent seat, when slide-off removal of the pump housing from the mounting clip is desired.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 8 is an inboard side elevational view of the mounting clip, shown with the medication infusion pump mounted thereon; and FIG. 9 is an enlarged fragmented sectional view taken generally on the line 9—9 of FIG. 8.

DETAILED DESCRIPTION OF THE PREFERRED EMBODIMENT

Figure 1:
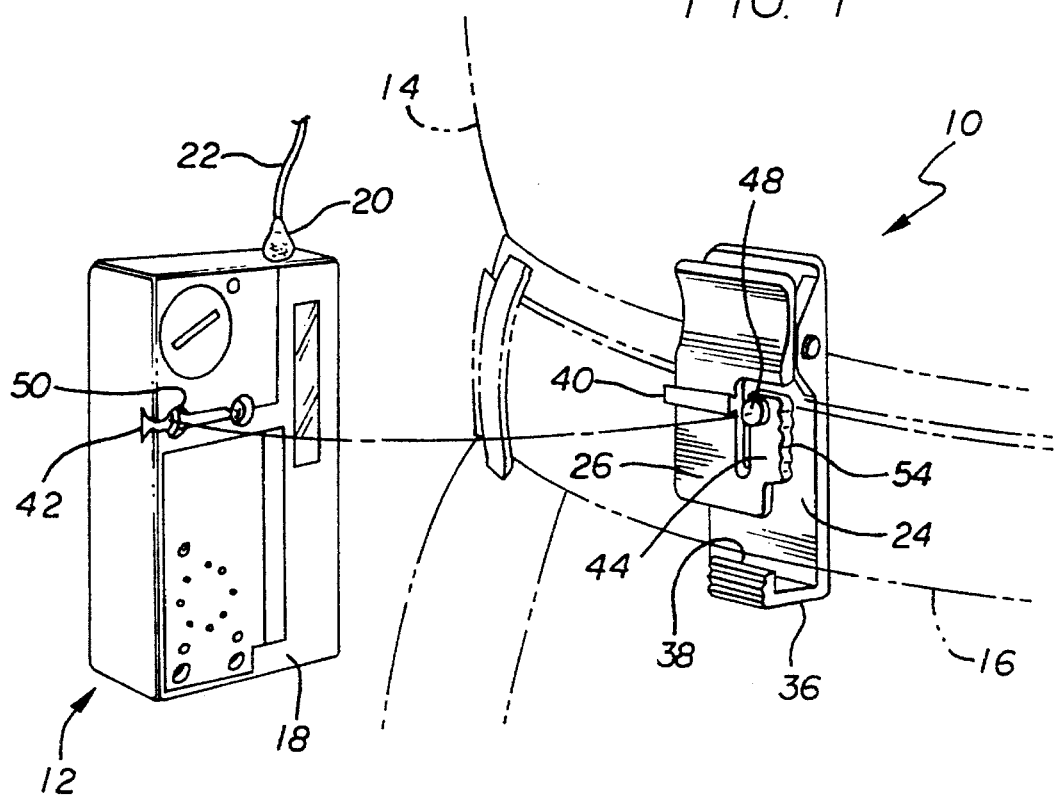
FIG. 1 is an exploded perspective view illustrating the improved mounting clip embodying the novel features of the invention, for use in removably supporting a medication infusion pump from the belt or the like of a patient.

As shown in the exemplary drawings, an improved mounting clip referred to generally in FIG. 1 by the reference numeral 10 is provided for removably supporting a medication infusion pump 12 on the body of a patient 14. The mounting clip 10 is particularly designed for mounting onto the patient's belt 16 or other convenient article of clothing. The mounting clip is adapted for smooth and safe mounting and dismounting of the infusion pump 12, without requiring disconnection of the pump from the patient or interruption in programmed delivery of medication such as insulin to the patient.

The medication infusion pump 12 has an overall construction and operation which is generally known in the art. As shown, the infusion pump 12 is provided in the form of a relatively compact housing 18 adapted to receive and support a syringe (not shown) or the like charged with a selected medication such as insulin to be administered to the patient 14. The pump 12 is operated in a precision preprogrammed manner to administer the medication via a luer fitting 20 (FIG. 1) and a catheter 22 to the patient, typically by use of an administration set of the type shown and described in U.S. Pat. No. 4,755,173. Medication infusion pumps of this general type are described in U.S. Pat. Nos. 4,562,751; 4,678,408; and 4,685,903, which are incorporated by reference herein. Such infusion pumps are available from MiniMed Technologies of Sylmar, Calif. under model designations 504 and 506.

The mounting clip 10 of the present invention provides an improved structure for receiving and supporting the medication infusion pump 12 from the patient's belt. The mounting clip 10 is designed for relatively simple yet secure mounting onto the patient's belt 16. Thereafter, the improved mounting clip 10 accommodates relatively easy and smooth slide-on mounting of the pump 12, without requiring any rapid or jerking motions which might otherwise pull upon the catheter 22 and potentially interfere with delivery of medication to the patient. The mounting clip securely and safely supports the infusion pump 12, with little or no risk of inadvertent separation of the pump from the mounting clip until removal therefrom is desired. The pump 12 is quickly and easily unlocked from the mounting clip with a simple fingertip motion to permit slide-off pump removal, again without requiring rapid or jerking movements.

Figure 2:
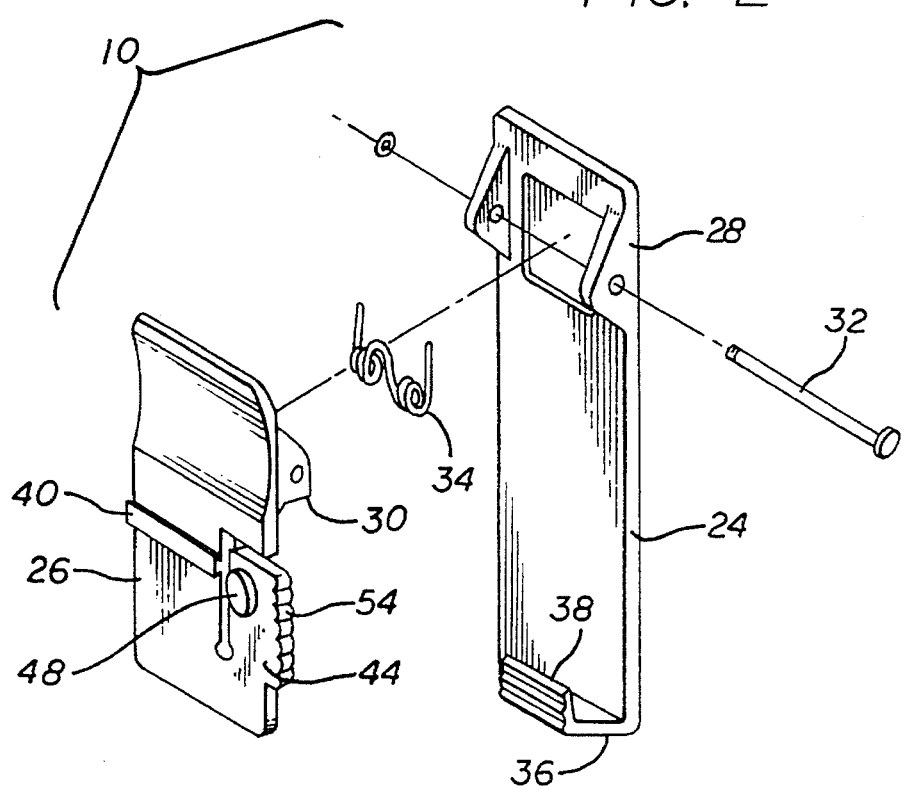
FIG. 2 is an enlarged exploded perspective view illustrating assembly of the mounting clip shown in FIG. 1.

As shown best in FIGS. 1 and 2, the preferred mounting clip comprises a belt clip with a pair of pivotally interconnected legs 24 and 26 which may conveniently be constructed from lightweight molded plastic. The two legs 24 and 26 include interfitting pairs of pivot brackets 28 and 30 near the upper ends thereof for receiving an interconnecting pivot pin 32. A torsion spring 34 is wrapped about the pivot pin 32 and has opposite ends engaging the legs 24 and 26 to springably urge the lower ends of the legs toward a normally closed position. As shown in FIG. 1, the leg 24 extends downwardly from the pivot pin 32 for a distance greater than the leg 26, and terminates in an outwardly turned lower foot 36 having an upturned toe 38 at the free end thereof. The brackets 28, 30 are shaped relative to each other to define stops which maintain the legs 24, 26 in generally parallel relation with each other in the normal closed position. The upper end of the toe 38 is spaced below the lower end of the second leg 26 to provide a space therebetween which accommodates slide-fit passage of the patient's belt 16.

Figure 7:
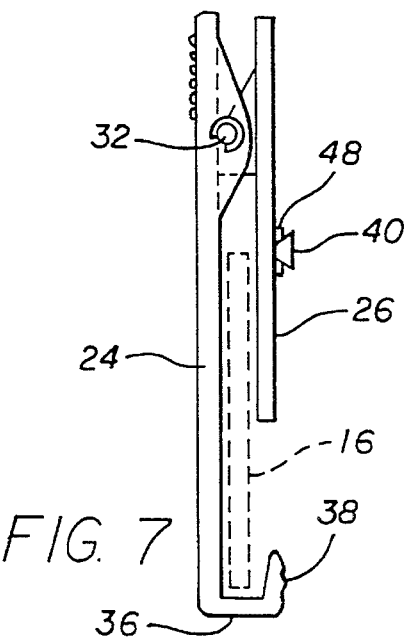
FIG. 7 is a side edge elevational view of the mounting clip, taken generally on the line 7—7 of FIG. 6.

The belt clip 10 is mounted quickly and easily onto the patient's belt by applying a manual fingertip squeeze force to the upper ends of the clip leg 24, 26, thereby spreading apart the lower ends of the belt clip legs. In this configuration, the leg 24 is inserted at the inboard side of the patient's belt 16, to fit the second leg 26 at the outboard side of the belt, at which time the fingertip pressure is released for spring return of the legs 24, 26 to parallel relation on opposite sides of the belt 16 (FIG. 7).

Figure 3:
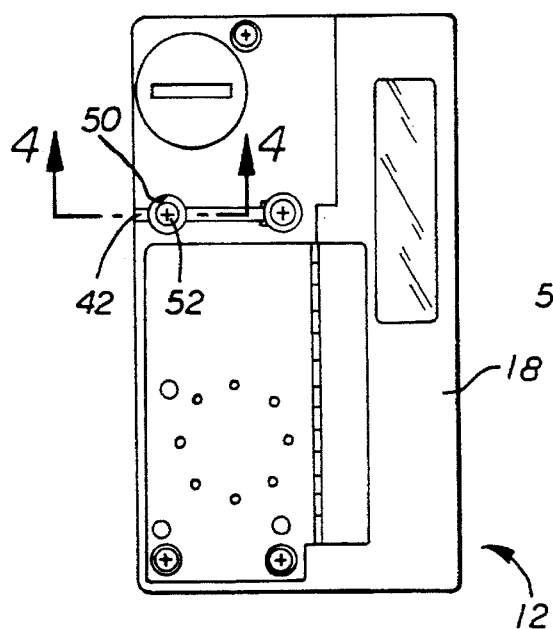
FIG. 3 is a rear elevation view of a medication infusion pump adapted for use with the mounting clip of the present invention.
Figure 4:
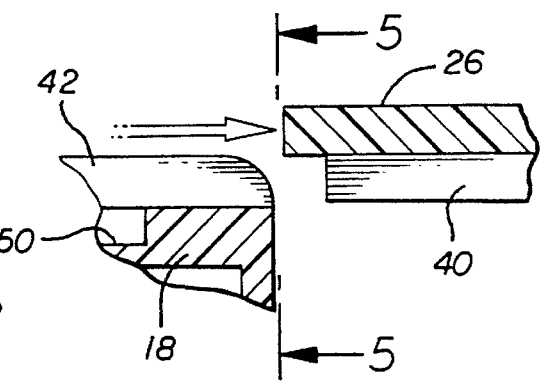
FIG. 4 is an enlarged fragmented sectional view taken generally on the line 4—4 of FIG. 3.
Figure 5:
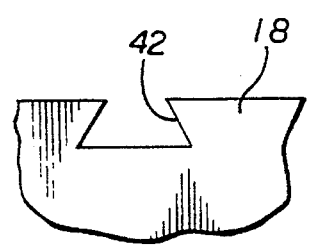
FIG. 5 is an enlarged fragmented sectional view taken generally on the line 5—5 of FIG. 4.

The outboard leg 26 of the belt clip 10 comprises a mounting plate for quick and easy removable mounting of the pump. More specifically, as shown, the leg 26 includes a dovetail key 40 shown to extend generally horizontally when the belt clip is mounted onto the patient's belt 16. This dovetail key 40 has a size and shape for slide-fit reception into and removal from a dovetail slot 42 (FIGS. 3, 5 and 9) formed in a rear wall of the pump housing 18. In this regard, the dovetail slot 42 extends from one side edge of the pump housing a short distance along the rear wall of the pump housing. The dovetail key is inserted into the dovetail slot by positioning the pump 12 adjacent the belt clip as viewed in FIG. 4, and then sliding the pump 12 in a direction to receive the dovetail key 40 fully into the slot 42.

Figure 6:
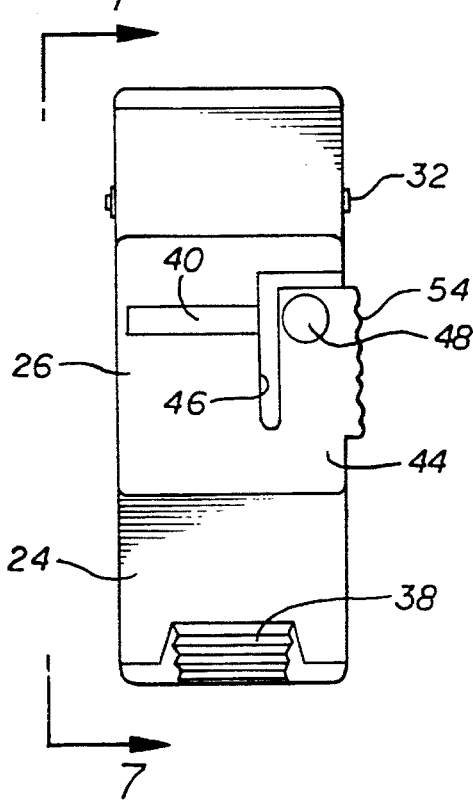
FIG. 6 is an enlarged outboard side elevational view of the mounting clip.

A spring arm 44 is integrally formed as part of the outboard leg 26. The spring arm 44 is separated from the dovetail key 40 by a narrow slot 46 (FIG. 6) to position a distal end of the spring arm 44 generally in alignment with the dovetail key 40. A detent button 48 which may have a round shape as shown in FIGS. 1 and 6, is positioned on the spring arm 44 for mating snap-fit reception into a detent seat 50 formed in the rear wall of the pump housing 18. In the preferred form, this detent seat 50 comprises a shallow counterbore which receives a mounting screw 52 (FIG. 9) used to assemble portions of the pump housing.

As the pump 12 is slide-on mounted onto the belt clip, the detent button 48 engages a rounded rear corner at one side edge of the housing 18 as the dovetail key 40 is advanced into the dovetail slot 42. The spring arm 44 has sufficient resilience to accommodate slight retraction of the detent button 48, to ride over the corner of the pump housing, until the key 40 is fully received into the slot 42 whereupon snap-fit alignment with the detent seat 50 is achieved. When such alignment occurs, the spring arm 44 advances the detent button 48 into the seat 50, for locking the pump 12 onto the belt clip 10. Importantly, this slide-on and snap-fit locking motion occurs easily and smoothly, with no requirement for any rapid or jerking motions. This mounting procedure is also accomplished easily as a one-handed operation, and without requiring significant visibility of the belt clip.

When the pump 12 is installed onto the belt clip, one side edge of the spring arm 44 defines a serrated segment 54 which protrudes a short distance beyond the adjacent side edge of the pump housing 18, as shown in FIG. 8. This serrated segment 54 has insufficient length to provide any significant risk of inadvertent spring arm retraction to release the detent button 48 from its seat 50. However, when pump removal is desired by the patient, the serrated segment 54 can be located quickly and easily, by tactile feel, and manually retracted with fingertip pressure to withdraw the detent button 48 from the seat 50. At the same time, slide-off movement of the pump 12 relative to the belt clip 10 is easily initiated with a one-handed motion to permit smooth slide-off removal of the pump 12 from the belt clip. Once again, no rapid or jerking movements are needed.

The improved mounting clip 10 of the present invention thus facilitates removable mounting of the medication infusion pump 12 onto the patient's belt 16, in a manner which is secure and stable and thus poses little or no risk to continued delivery of medication to the patient.

A variety of modifications and improvements to the improved mounting clip 10 of the present invention will be apparent to those skilled in the art. For example, it will be understood that the outboard leg 26 of the belt clip 10 can be associated with alternative means for mounting onto the patient's belt or any other article of clothing, so as to position the leg 26 for slide-fit and detent snap-fit assembly with the housing 18 of the pump 12. Accordingly, no limitation on the invention is intended by way of the foregoing description and accompanying drawings, except as set forth in the appending claims.

What is claimed is:

1. A mounting clip for removably supporting a medication infusion pump on a patient, said mounting clip comprising:

a mounting plate having slide-fit means including a dovetail key formed on said mounting plate for slide-on mounting and slide-off removal of the pump with respect to said plate, and detent means for locking the pump on said plate when the pump is slidably mounted thereon;

said detent means being manually releasable to permit slide-off removal of the pump from said plate; and means for mounting said plate onto a patient.

2. The mounting clip of claim 1 wherein said detent means comprises a spring arm carried by said plate and having a detent buttom generally at a distal end of said spring arm.

3. The mounting clip of claim 2 wherein said plate and spring arm are integrally formed.

4. The mounting clip of claim 2 wherein said plate and spring arm are formed from molded plastic.

5. The mounting clip of claim 1 wherein said mounting means is adapted for removable mounting of said plate onto a selected article of clothing worn by the patient.

6. The mounting clip of claim 1 wherein said mounting means comprises a leg member pivotally interconnected to said mounting plate whereby said mounting plate and leg member cooperatively define a belt clip for removable mounting onto a belt worn by the patient.

7. The mounting clip of claim 1 wherein said detent means includes a spring arm defining a detent member thereon, said spring arm further defining an edge surface protruding outwardly beyond the pump when said pump is mounted and locked onto said mounting plate, said edge surface being manually accessible to retract said spring arm relative to the pump to manually release said detent means.

8. The mounting clip of claim 7 wherein said edge surface of said spring arm is a serrated edge.

9. A mounting clip for removably supporting a medication infusion pump on a patient, said mounting clip comprising:

a mounting plate having a dovetail key thereon for slide-fit reception into a dovetail slot formed in a housing of the medication infusion pump;

said mounting plate further including a spring arm having a detent button thereon for snap-fit reception into a detent seat formed in the pump housing when said dovetail key is substantially fully received into the dovetail slot, whereby the pump housing is slidably mountable onto said mounting plate and locked thereon upon snap-fit reception of said detent button into the detent seat, said spring arm being positioned for manual retraction relative to the pump housing to retract said detent button from the detent seat and thereby permit slide-off removal of the pump housing from said mounting plate; and means for mounting said plate onto an article of clothing worn by a patient.

10. The mounting clip of claim 9 wherein said plate and spring arm are formed from molded plastic.

11. The mounting clip of claim 9 wherein said mounting means comprises a leg member pivotally interconnected to said mounting plate whereby said mounting plate and leg member cooperatively define a belt clip for removable mounting onto a belt worn by the patient.

12. The mounting clip of claim 9 wherein said spring arm further defines an edge surface protruding outwardly beyond the pump when said pump is mounted and locked onto said mounting plate, said edge surface being manually accessible to retract said spring arm relative to the pump to manually release said detent means.

13. In combination:

a medication infusion pump for delivery of a selected medication to a patient, said pump including a pump housing; and a mounting clip for mounting onto the patient and including a mounting plate;

said mounting plate and pump housing defining interengageable slide-fit means including a dovetail key formed on one of said pump housing and mounting plate, and a matingly shaped dovetail slot formed on the other of said pump housing and mounting plate, said slide-fit means being for slide-on mounting and slide-off removal of the pump housing with respect to said mounting plate;

said mounting plate and pump housing further defining interengageable detent means for snap-fit locking of the pump housing onto said mounting plate when said slide-fit means is substantially fully engaged;

said detent means being manually releasable by the patient to unlock the pump housing from said mounting plate and permit slide-off removal therefrom.

14. The combination of claim 13 wherein said detent means comprises a detent button formed on one of said pump housing and mounting plate, and a mating detent recess formed on the other of said pump housing and mounting plate.

15. A mounting clip for removably supporting a medication infusion pump on a patient, said mounting clip comprising:

a mounting plate having slide-fit means for slide-on mounting and slide-off removal of the pump with respect to said plate, and detent means for locking the pump on said plate when the pump is slidably mounted thereon;

said detent means beging manually releasable to permit slide-off removal of the pump from said plate; and means for mounting said plate onto a patient;

said detent means on said mounting plate comprising a spring arm having a detent member thereon, said spring arm defining an edge surface protruding outwardly beyond the pump housing when said pump housing is mounted and locked onto said mounting plate, said edge surface being manually accessible to retract said spring arm relative to the pump housing to manually release said detent means.

16. The combination of claim 15 wherein said edge surface of said spring arm is a serrated edge.

17. A mounting clip for removably supporting a medication infusion pump on a patient, said mounting clip comprising:

a mounting plate having slide-fit means for slide-on mounting and slide-off removal of the pump with respect to said plate, and detent means for locking the pump on said plate when the pump is slidably mounted thereon;

said detent means beging manually releasable to permit slide-off removal of the pump from said plate; and means for mounting said plate onto a patient;

said slide-fit means comprising an open-ended dovetail slot formed in the pump housing and a mating dovetail key formed on said mounting plate, and wherein said detent means comprises a detent recess formed in said pump housing at a position generally in-line with said dovetail slot and a spring arm forming a portion of said mounting plate and having a detent button for snap-fit reception into said detent recess.

18. The combination of claim 17 wherein said pump housing comprises at least two housing members assembled to each other by at least one mounting screw, said mounting screw being received in a counterbore formed in one of the housing members, said counterbore defining said detent recess.

19. A mounting clip for removably supporting a medication infusion pump on a patient, said mounting clip comprising:

a mounting plate having slide-fit means for slide-on mounting and slide-off removal of the pump with respect to said plate, and detent means for locking the pump on said plate when the plate is slidably mounted thereon;

said detent means being manually releasible to permit slide-off removal of the pump from said plate; and means for mounting said plate onto a patient;

said detent means including a spring arm defining a detent member thereon, said spring arm further defining an edge surface protruding outwardly beyond the pump when said pump is mounted and locked onto said mounting plate, said edge surface being manually accessible to retract said spring arm relative to the pump to manually release said detent means.

20. The mounting clip of claim 19 wherein said edge surface of said spring arm is a serrated edge.

* * * * *